(12) United States Patent
Clark

(10) Patent No.: US 7,767,071 B1
(45) Date of Patent: Aug. 3, 2010

(54) DIELECTRIC AND CONDUCTIVE IMAGING APPLIED TO GEL ELECTROPHORESIS

(76) Inventor: Lloyd Douglas Clark, 15 Conrad St., San Francisco, CA (US) 94131

( * ) Notice: Subject to any disclaimer, the term of this patent is extended or adjusted under 35 U.S.C. 154(b) by 918 days.

(21) Appl. No.: 11/355,549

(22) Filed: Feb. 16, 2006

Related U.S. Application Data

(60) Provisional application No. 60/653,572, filed on Feb. 16, 2005.

(51) Int. Cl.
*G01N 27/26* (2006.01)
(52) U.S. Cl. .......... 204/600; 204/606; 204/607; 204/608; 204/450; 204/461
(58) Field of Classification Search ......... 204/450–477, 204/600–650, 400–435
See application file for complete search history.

(56) References Cited

U.S. PATENT DOCUMENTS

| | | | | |
|---|---|---|---|---|
| 5,073,963 | A * | 12/1991 | Sammons et al. | 382/128 |
| 5,194,133 | A * | 3/1993 | Clark et al. | 204/608 |
| 6,265,883 | B1 | 7/2001 | Clark | |
| 6,653,091 | B1 * | 11/2003 | Dunn et al. | 435/14 |
| 2003/0012693 | A1 * | 1/2003 | Otillar et al. | 422/58 |

FOREIGN PATENT DOCUMENTS

WO   WO02025052   *  7/2002

* cited by examiner

*Primary Examiner*—Alexa D Neckel
*Assistant Examiner*—Jennifer Dieterle

(57) ABSTRACT

A system for displaying the positions of substances in electrophoretic separations comprises a gel (635) a substance to be separated into a region (450), plates (400, 401) with electrodes (405-420 and 430-445) placed on either side of the gel. A source (315) applies a voltage to an electrode on one side of the gel, and an electrode on the other side of the gel is connected to the input of an amplifier (320). Multiplexers (605, 610) connect the source and amplifier to electrodes on either side of the gel. A computer (600) issues commands to the multiplexers to connect the source and amplifier to individual electrodes, and while a pair of electrodes is so connected, the computer activates a sample-and-hold circuit (620) and an A/D converter (630) to record the value of the electrical impedance within the gel at the location of the selected electrodes. The impedance value is stored in the computer's memory and also displayed on a monitor (635) connected to the computer. The result is visualization of a gel-electrophoretic separation without requiring the use of stains, radioactivity, or molecular tags.

15 Claims, 6 Drawing Sheets

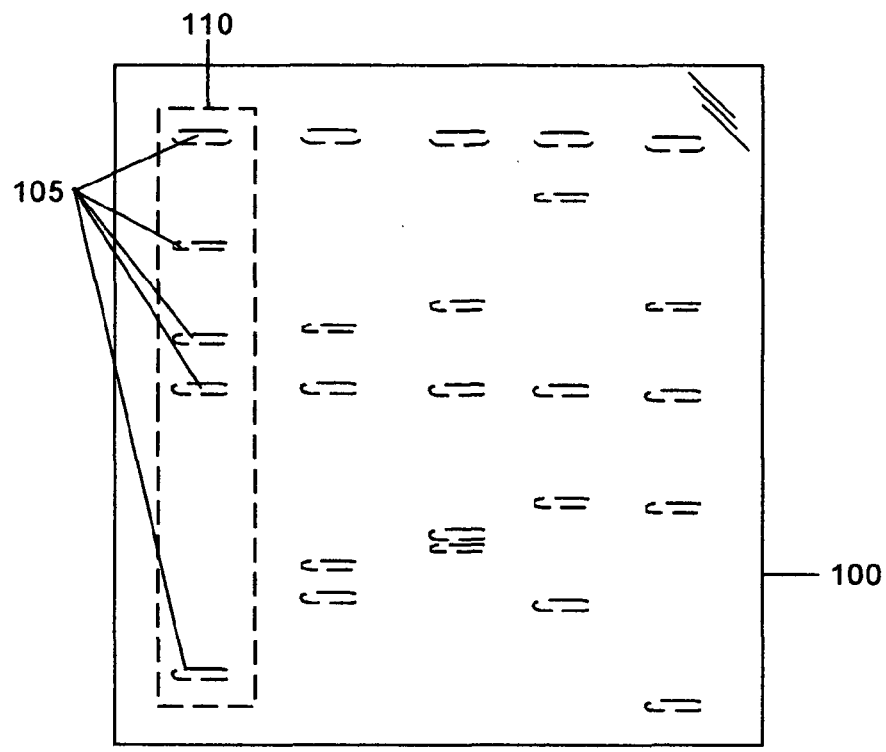
Fig. 1--Prior-Art
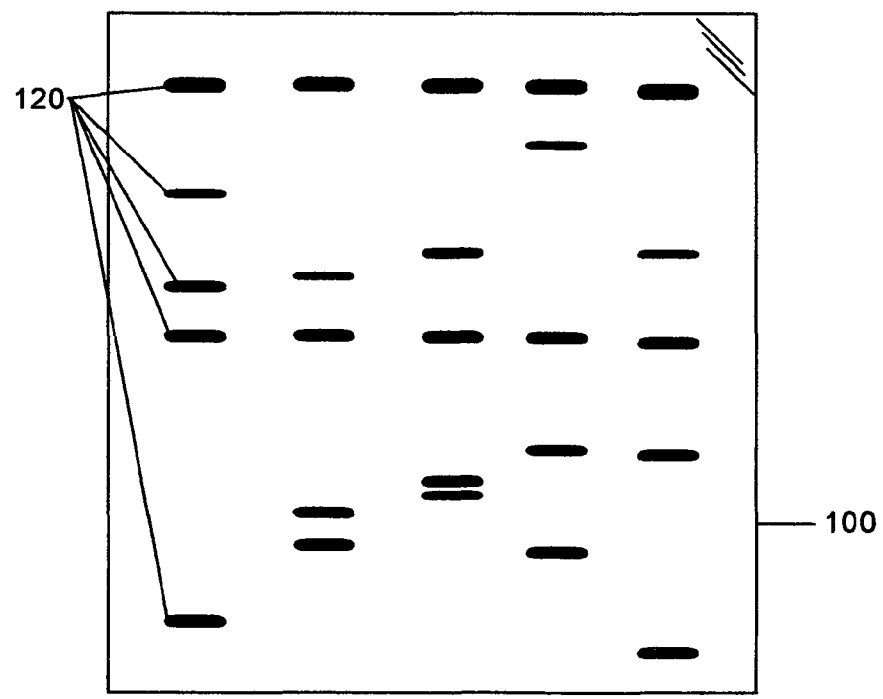
Fig. 2--Prior-Art

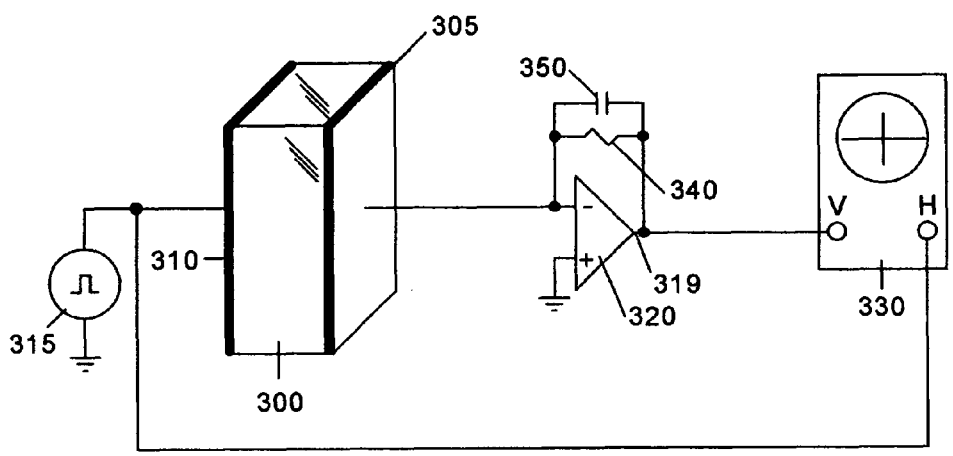
Fig. 3--Prior-Art
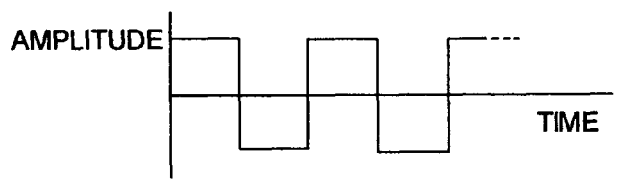
Fig. 4--Prior-Art
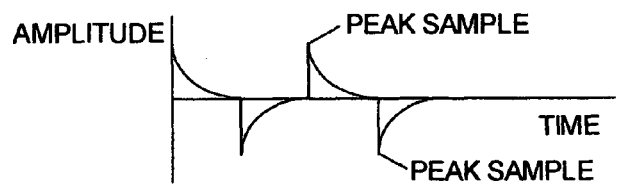
Fig. 5--Prior-Art
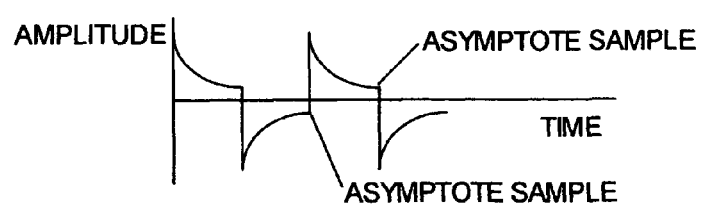
Fig. 6--Prior-Art

DIELECTRIC AND CONDUCTIVE IMAGING APPLIED TO GEL ELECTROPHORESIS

CROSS-REFERENCE TO RELATED APPLICATION

This patent is based on an application that claims priority of provisional patent application Ser. No. 60/653,572, filed Feb. 16, 2005.

BACKGROUND

1. Field

The field is electrophoretic separations, and in particular to their visualization and analysis.

2. Prior Art—Protein Separations—FIGS. 1-2

The individual components of protein mixtures, such as those with different molecular weights, often must be separated in order to determine the relative quantities of each within the mixture. Separations of the proteins within cells are useful in comparing diseased and healthy tissue samples, for example. In the past, such components were separated according to their molecular weight using gel-electrophoresis in well-known fashion. A number of gel materials were used to elute or draw out the components according to their molecular weights. One such gel was polyacrylamide. A clear gel 100, as shown in FIG. 1, typically had an area about 100 cm² and thickness 1.0 mm. Smaller and larger, thicker and thinner gels have been used. Other gels and methods have been used to separate amino acids and other compounds.

After separation, gel 100 was generally transparent and devoid of color. Protein components 105 typically reside within lanes, one of which is indicated by a dashed outline 110. Several means have been used to visualize the as yet invisible separated protein components 105, indicated by dashed lines. In one method of visualization, components 105 are made visible by immersing the gel in a stain such as Comassie blue, silver, and others.

After staining, FIG. 2, previously invisible components 105 (FIG. 1) were visible and were seen as darker regions 120 within gel 100. Gel 100 absorbed very little of the stain. The position of each of regions 120 was analyzed to reveal the molecular weight of the corresponding component 105. Their extent and optical density revealed the volume of protein component 105 within each band.

Instead of staining after separation, stains, fluorescent materials, or radioactive tags can be applied to components 105 prior to separation.

While staining is well-known, it is cumbersome and time-consuming. Radioactive tagging presents a safety and disposal hazard. Incorporating a stain or fluorescent molecule prior to separation can change the molecular weight of the material being analyzed, thereby causing errors in analysis. In addition, gels are very fragile and they must be handled carefully during staining and analysis, or they will separate or tear.

Prior-Art—Dielectric Constant Measurement—FIGS. 3-5

A brief discussion about electrical measurements used in the present invention follows. The dielectric constant of a volume of insulating or semi-insulating material 300 (FIG. 3) can be measured using an electrical circuit. Electrodes 305 and 310 are placed in contact with material 300. A voltage source 315 is connected to electrode 310. The inverting input of an operational amplifier 320 is connected to electrode 305. The non-inverting input of amplifier 320 is connected to ground return, as is the second terminal of source 315. The output terminal 319 of amplifier 320 is connected to the vertical input, indicated by "V" in FIG. 3, of an oscilloscope 330. The horizontal time base, "H", of oscilloscope 330 is triggered by the output of source 315. Resistor 340 and capacitor 350 determine the gain of amplifier 320 in well-known fashion. With resistor 340 and capacitor 350 in place, the inverting input of amplifier 320 is maintained at ground potential in the circuit shown. Linear operation of amplifier 320 is assumed. Instead of oscilloscope 330, other circuitry can be used including a peak detector, microprocessor, and the like, in well known fashion.

Assume that the volume of material 300 is 0.5 mm thick between electrodes 305 and 310, and that its area is 2 mm². Neglecting edge effects, the capacitance of the volume of material 300 is given by the formula below.

$$C = \frac{\varepsilon A}{d}$$

$\in$ is the dielectric constant of volume 300, A is the area of electrodes 305 and 310, and d is the thickness of volume 300. $\in$ is generally represented as the product of $\in_o$, the permittivity of vacuum, and $\in_r$, the relative dielectric constant of the material under study. The value of $\in_0$ is $8.85\times10^{-12}$ Farad/m. If $\in_r$ of the material in volume 300 is 20, then $C_v = 7\times10^{-1}$ picofarads (pf).

If source 315 provides a square wave, as shown in FIG. 4, the output of amplifier 320 will be a transient peak, followed by a decay, as shown in FIG. 5. The rate of decay is determined by resistor 340 and capacitor 350. The associated time constant is equal to the product of the values of resistor 340 and 350. If the value of resistor 340 is one megohm (1 MΩ), and the value of capacitor 350 is 1 pf, then the decay time constant is one microsecond (μS). If a period of ten time constants is allowed to elapse between pulses, then the maximum frequency of the applied square wave is 50 kHz.

If the volume in material 300 is insulating, the steady-state gain of amplifier 320 will be unity. The transient gain is given by the ratio of the capacitance of the material in volume 300 and the capacitance of capacitor 350. If the value of capacitor 350 is 5 pf, then the gain of amplifier 320 is 0.7 pf/5 pf=0.14. Therefore if the voltage output of source 315 is 10 volts (V) peak-to-peak (p-p), the output of amplifier 320 will be 1.4 V p-p.

Electrical Conductivity Measurement—FIGS. 3, 4, and 6

The above circuitry can be used to measure the electrical conductivity of the volume in material 300. Instead of measuring the peak-to-peak value as described above (FIG. 5), the direct-current (DC) value or asymptote is measured (FIG. 6). At the asymptote the current density in material 300 is given by $$j = \sigma E,$$

where j=the current density in amperes per square cm, σ=the conductivity in Siemens/mm (S/mm), and E is the amplitude of the electric field applied between electrodes 305 and 310 in V/mm.

As above, assume that the volume of material 300 is 0.5 mm thick between electrodes 305 and 310, that its area is 2 mm². Further, assume that the applied voltage is 10 V, and that the asymptotic value of the current (FIG. 6) is $10^{-9}$ A. The conductivity of material 300 is thus $0.5\times10^{-10}$ S/mm.

In summary, FIG. 4 represents the output of source 315. FIG. 5 represents the output of amplifier 320 when the electrical properties of the contents of volume 300 are mainly capacitive. FIG. 6 represents the output of amplifier 320 when the contents of volume 300 have a mixture of capacitive and resistive properties.

Instead of using square-wave voltage source 315, a sinusoidal source (not shown) can be used in well-known fashion. The mathematics used in analysis of signals excited by a sinusoidal source is described in detail in my U.S. Pat. No. 6,265,883 (2001) which is incorporated herein by reference.

ADVANTAGES

Accordingly, one advantage of one or more aspects of the present invention is to provide a system and method for visualizing electrophoretic separations with or without the use of stains, radioactivity, or fluorescent materials. Another advantage of one or more aspects of the present invention is to provide a system and method for visualizing electrophoretic separations in progress. Further advantages will become apparent from a study of the following figures and their descriptions.

SUMMARY

In accordance with a preferred embodiment of the present invention, an imaging system provides visualization of electrophoretically-separated components within a gel by virtue of their capacitive or conductive properties, without the use of stains, fluorescent materials, or radioactive tags. In a second embodiment, the imaging system provides visualization of the separation of components in real-time, as it is occurring during electrophoresis.

DRAWING FIGURES

FIG. 1 shows a prior-art electrophoresis gel after separation, and before staining.

FIG. 2 shows the prior-art gel of FIG. 1 after staining.

FIG. 3 is an electronic schematic diagram of a prior-art system for measuring dielectric constant or electrical conductivity.

FIG. 4 is an amplitude-vs.-time plot of voltage from source 315 in FIG. 3.

FIG. 5 is an amplitude-vs.-time plot of the voltage output of amplifier 320 in FIG. 3 as it relates to dielectric constant measurements.

FIG. 6 is an amplitude-vs.-time plot of the voltage output of amplifier 320 in FIG. 3 when material 300 has a finite electrical conductivity.

DRAWING FIGURE REFERENCE NUMERALS

100 Gel
105 Band
110 Lane
120 Band
300 Sample material
305 Electrode
310 Electrode
315 Source
319 Output terminal
320 Amplifier
330 Oscilloscope
340 Resistor
350 Capacitor
400 Plate
401 Plate
405-420 Electrodes
421 Electromagnetic shield
430-445 Electrodes
450 Lane
455-470 Wires
475-490 Wires
600 Computer
605 Multiplexer
610 Multiplexer
620 Sample-and-hold
630 A/D converter
635 Monitor
7900-708 Spots
800 Insulator
805 Insulator
901-908 Connection line
1100-1175 Blocks

First Embodiment

Figure 7:
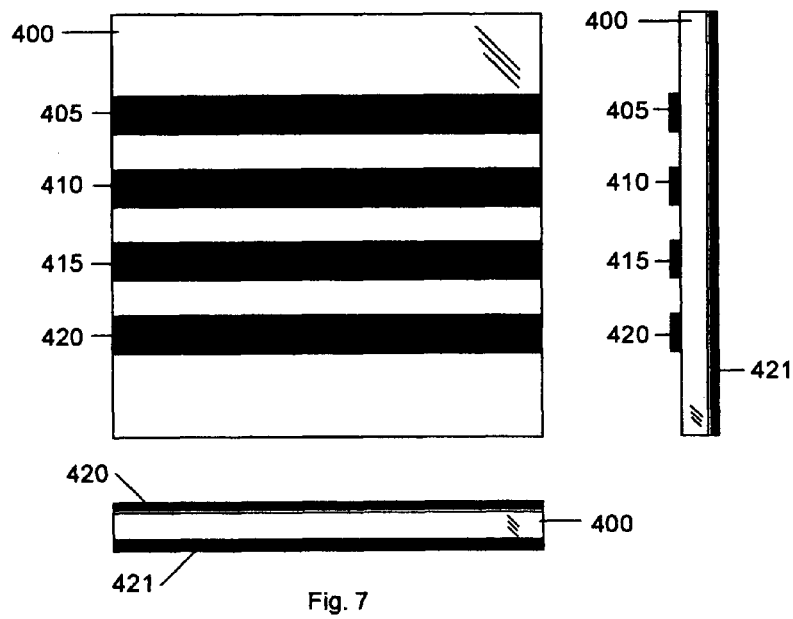
FIG. 7 shows an electrode arrangement according to a first embodiment of the instant invention.
Figure 8:
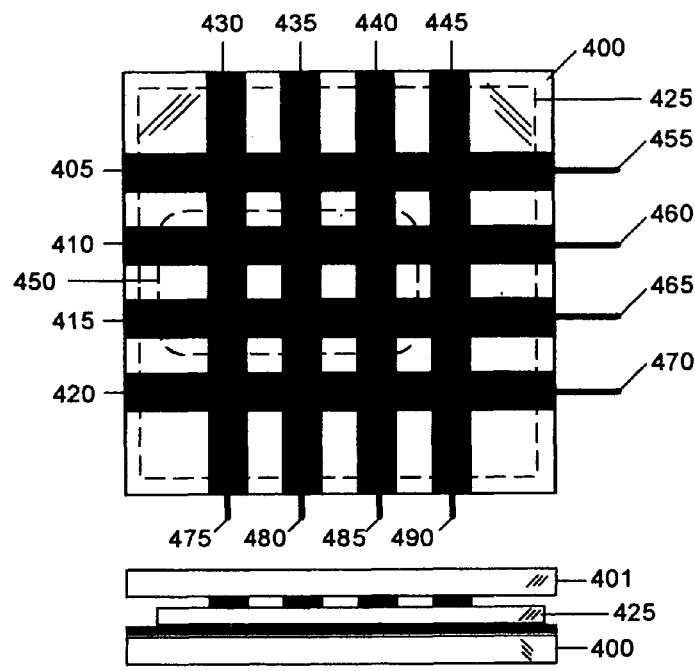
FIG. 8 shows a sandwich of plates, electrodes, and gel according to the present invention.

Used after Separation—Description—FIGS. 7 and 8

In this discussion, it is assumed that an electrophoretic molecular separation of the components of a protein mixture, for example the proteins from the cells in a tissue sample, has occurred. The proteins were previously placed along the top edge of the gel, and an electric field was applied between the top and bottom edges of the gel to cause the proteins to migrate downward in the gel, in well-known fashion. The proteins were separated according to their molecular weights, the lower molecular weight components moving faster through the gel than those with higher molecular weights.

The gel has been removed from the separation apparatus. At this time, the separated components of the mixture cannot be seen within the gel.

Insulating plates or sheets 400 (FIG. 7) are fitted with electrodes 405-420. Insulating sheet 400 is preferably glass, about two mm thick. It can also be a rigid or semi-rigid plastic. Sheet 400 may be of any square or rectangular area from about one centimeter on a side to twenty or more centimeters on a side.

A number of linear conductors are placed on a first side of sheet 400. Although four are shown, there can be from one to many thousand conductors. Conductors 405-420 are preferably made of an electrically conductive material such as indium-tin-oxide (ITO). ITO is very rugged and scratch resistant. It is also transparent. Alternatively, a metal can be used.

An optional, electrically conductive, electromagnetic shield 421 (FIG. 7) can the applied to the second side of sheet 400. When properly grounded, shield 421 will reduce electrical interference from outside sources and make the present measurement, described below, more sensitive. In the side views of FIGS. 7 and 8, the thickness of conductors 405-420 and 430-445 is exaggerated to make them visible. The thickness of conductors 405-420 is preferably less than twenty microns. Conductors 405-420 preferably extend from one edge of sheet 400 to the other. They are about 1 mm wide and spaced by 1 mm. Other dimensions are acceptable. The width is determined by a compromise between two factors. On one hand, higher resolution scans (discussed below) require smaller widths and spacings. On the other hand, sensitivity increases with greater widths, and undesirable crosstalk (discussed below) decreases with greater spacings.

Sheets 400 are used in pairs, as shown in FIG. 8. Two insulating plates or sheets 400 and 401 are provided with electrodes comprising conductors 405-420 and 430-445.

In use, a gel 425 is sandwiched between two similar, orthogonally-disposed sheets 400 and 401 (FIG. 8). Electrodes 405-420 are in contact with one-side of gel 425. Electrodes 430-445 are in contact with the opposite side of gel 425. Connecting wires 455-490 connect electrodes 405-420 and 430-445 to external circuitry, described below.

The locus of a band or spot 450 in gel 425 is indicated by dashed line around spot or region 450. A certain fraction of the material under study has moved to this location in gel 425 after separation. Although the material in band 450 is not visible, a latent image is present in the form of a raised dielectric constant or changed electrical conductivity in gel 425.

During separation, the matrix comprising gel 425 is immobile. The materials that were separated during electrophoresis have moved through gel 425, leaving groups of proteins in certain locations, such as indicated at band 450. Gel 425 has a constant or nearly constant value of dielectric constant or conductivity over its entire volume. (Non-isotropic gradient gels are discussed below.) The separated substance in band 450 has its own associated value of dielectric constant or conductivity.

A capacitor is formed in the region in gel 425 between conductors. For example, a first capacitor is located at the crossing of electrodes 405 and 430. A second one is at the crossing of electrodes 410 and 440, and so forth. The first capacitor (405-430) lies outside band 450. The second capacitor (410-440) lies within the region of band 450. The capacitance of the first capacitor is dependent upon the material in gel 425. The capacitance of the second capacitor is dependent upon the material in gel 425 and the material in band 450. Since the material in gel 425 is immobile, the dielectric constant of the material in band 450 additively combines to yield a new dielectric constant in band 450. The value of the new dielectric constant is dependent upon the concentration of material in band 450.

For example, if the dielectric constant of gel 425 is 20, a first capacitance value will result between electrodes 405 and 430, and all other electrodes lying outside band 450. If the dielectric constant of the material in band 450 is also 20 and the volume concentration of this material is 0.1% relative to gel 425, then the capacitance value between electrodes 410 and 440, and all other electrodes within region 450, will be increased by 0.1%. It is this difference that will be detected, as described below.

Similarly, electrical conductivity in the region of band 450 can be different from that of gel 425. This difference can be detected, as described above in connection with FIG. 6. It is displayed as described above.

First Embodiment

Figure 9:
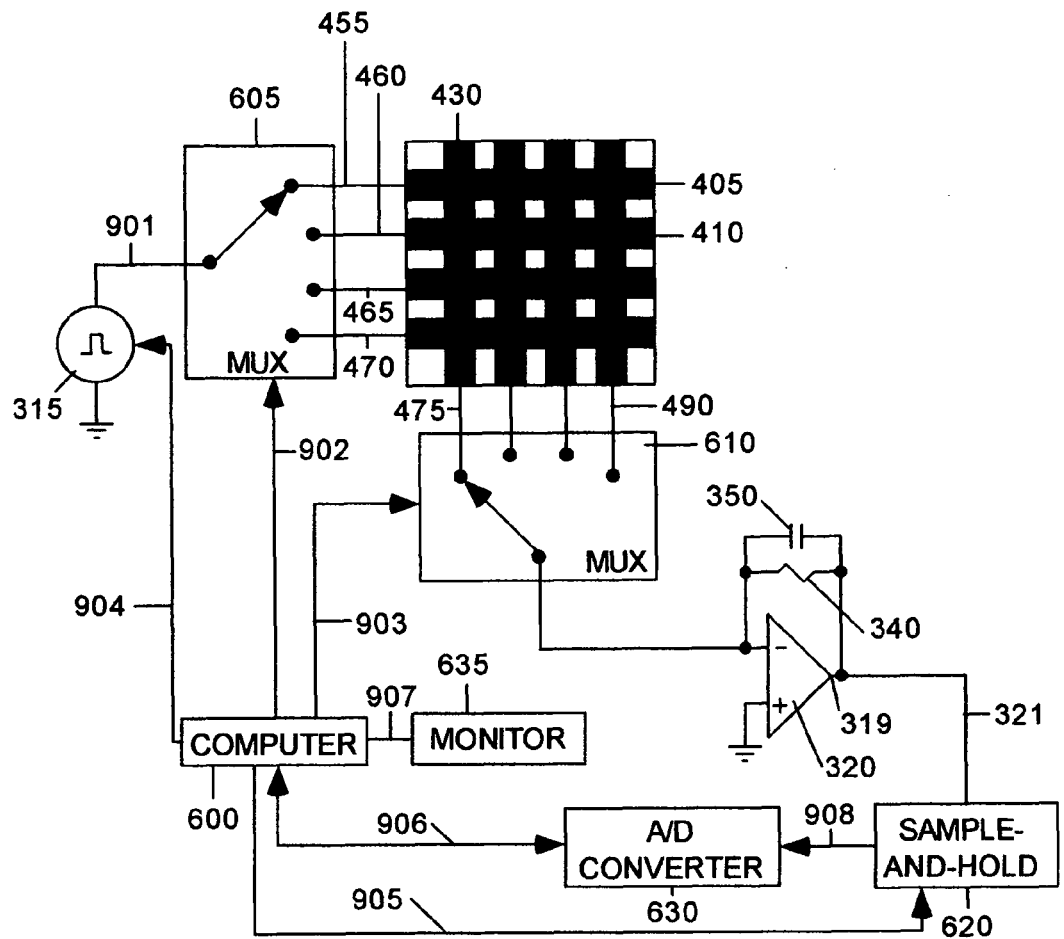
FIG. 9 shows the sandwich of FIG. 8 connected to electronic circuitry for analysis.
Figure 10:
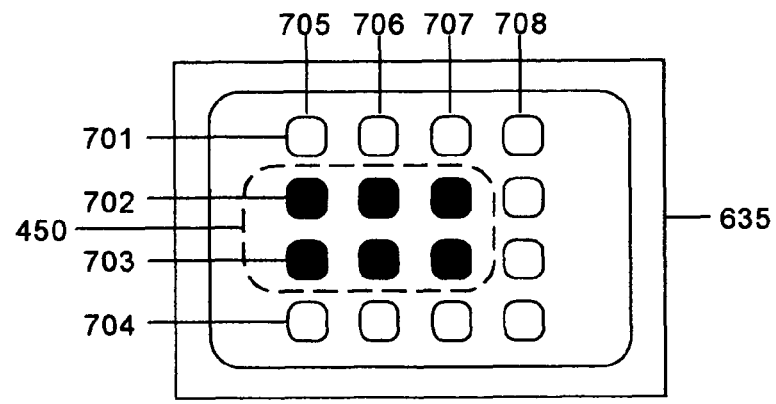
FIG. 10 shows a separated band in a gel according to the present invention.
Figure 11:
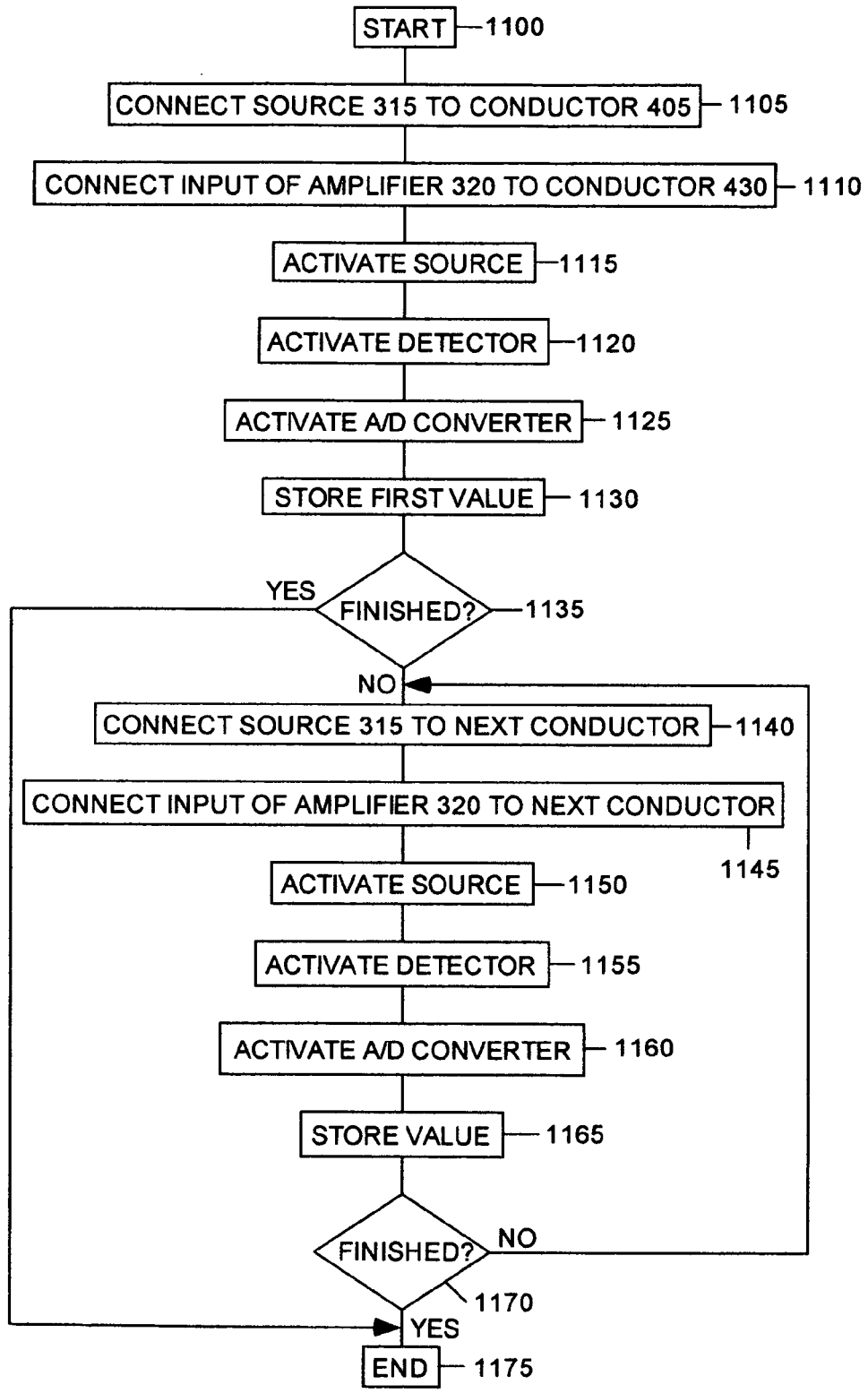
FIG. 11 is a flow chart depicting the operation of a first embodiment.

Operation—FIGS. 9-11

The elements of FIG. 5 are connected into an electrical circuit as shown in FIG. 9. The circuit comprises a computer 600, multiplexers 605 and 610, a sample-and-hold circuit 620, an analog-to-digital (A/D) converter 630, and operational amplifier 320, with resistor 340, and capacitor 350. In the event only one electrode is used in each direction, multiplexers 605 and 610 reduce to a simple connection between their input and output terminals, i.e. a wire connection replaces each multiplexer.

One terminal of multiplexer 605 is supplied with a signal from source 315 via connection line 901. Under commands via line 902 from computer 600, multiplexer 605 connects source 315 to connections 455-470, one-at-a-time. Multiplexers 605 and 610 are preferably arranged to connect unconnected inputs and outputs to signal ground return in order to reduce unwanted crosstalk between conductors 430-445 and 405-420.

Using line 902, computer 600 instructs multiplexer 605 to connect source 315 to conductor 405 via connection 455. Using line 903, computer 600 also instructs multiplexer 610 to connect the inverting input of amplifier 320 to conductor 430 via wire connection 475. With these connections made, computer 600 uses line 904 to activate source 315 to supply a pulse or square-wave signal, similar to that shown in FIG. 4, to multiplexer 605. The capacitor formed across gel 425 in the region directly between electrodes 405 and 430 couples this signal to the inverting input of amplifier 320. Output 319 of amplifier 320 provides a signal to a sample-and-hold circuit 620 via line 321. In the present case, the operation of sample-and-hold circuit 620 is timed by computer 600 to capture the peak value of the voltage waveform in FIG. 5. Using line 905, computer 600 activates sample-and-hold circuit 620 to sample this value and hold it on line 908 while computer 600 activates A/D converter 630, via line 906, to convert the value to a digital representation. This digitized value is then stored in the memory (not shown) of computer 600.

Using line 902, computer 600 next instructs multiplexer 605 to disconnect source 315 from connection 455, and then to connect source 315 to connection 460. Using line 904, computer 600 next instructs source 315 to provide a signal, which is delivered to connection 460. The above sequence of signal interpretation is repeated, only this time a digitized value representative of the capacitance in the region between electrodes 430 and 410 is obtained.

This series of events continues until voltages representative of the values of all capacitances in the regions between all electrodes have been measured, digitized, and stored.

A display monitor 635, connected to computer 600 via line 907, displays the above data, as shown in FIG. 10. An X-Y grid of spots or areas 701-708 is shown on monitor 635. These are arranged to conform to the locations of the overlaps of electrodes 405-420 and 430-445. For example, the spot at row 701, column 705 displays a spot image whose gray value is proportional to the capacitance between electrodes 405 and 430. The dark spots at the intersections of rows 702-703, with columns 705-707, indicate the presence of a dielectric constant greater than that of the gel. These spots lie within the region of band 450 (FIG. 8). A different gray value is shown at the locations adjacent band 450. Thus a humanly sensible image of bands 450 in gel 425 is displayed on monitor 635. Computer 600 can cause other humanly sensible indicia to be reported, such as a sound that emanates from computer 600 when a portion of the separation reaches a certain location on the gel, alternative or additional programmatic steps, and the like.

Thus the system displays and compares the dielectric constants of the gel and the material contained in volume 450. The gel containing the separation is imaged without the use of stains, radioactive, or fluorescent materials. It is still possible to stain the gel, if desired, since the above procedure does not disturb the positions of the bands of material.

Measurements of electrical conductivity between electrodes can be made in a manner similar to that for determining dielectric constants. In the case of conductivity, the operation of sample-and-hold 620 is timed to lie within the asymptote of the voltage output of amplifier 320. This is shown in FIG. 6. The rest of the description remains the same as for dielectric differences.

A flowchart depicting the operation described above is shown in FIG. 11. The flowchart starts at block 1100. Computer 600 first instructs multiplexer 605 to connect source 315 to conductor 405 (block 1105). Computer 600 then instructs multiplexer 610 to connect the input of amplifier 320 to conductor 430 (block 1110). Computer 600 then activates source 315, sample-and-hold circuit 620, and A/D converter 630, in turn (blocks 1115, 1120, and 1125, respectively). The first value obtained by converter 630 is stored in the memory of computer 600 (block 1130).

If there is only one electrode 405 in use on plate 400, and one electrode 430 in use on plate 401, the task is finished (block 1135) and flow proceeds to the end (block 1175).

If more electrodes are used, source 315 is connected to the next conductor on plate 400 (block 1140), the input of amplifier 320 is connected to the next conductor on plate 401 (block 1145), source 315 is activated (block 1150), sample-and-hold 620 is activated (block 1155), A/D converter 630 is activated (block 1160), and the value measured by A/D converter 630 is stored in the memory of computer 600 (block 1165).

This process repeats (block 1170) until the signals from all conductors have been stored in the memory of computer 600. This ends the process (block 1175).

Second Embodiment

Figure 12:
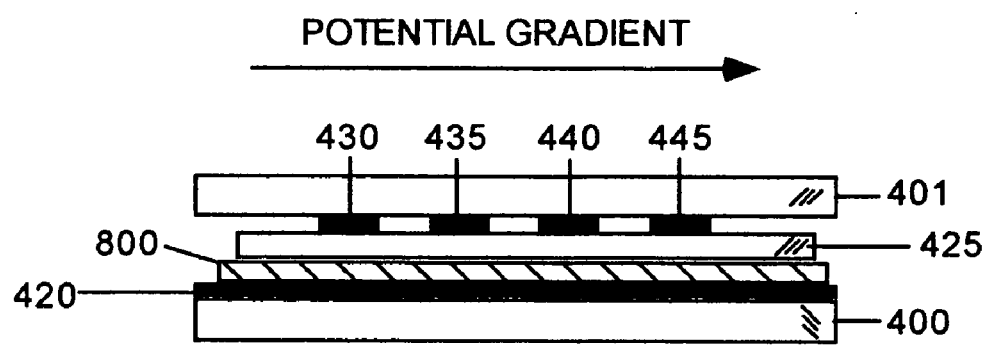
FIGS. 12 and 13 show placements of insulators in one aspect of a second embodiment.
Figure 13:
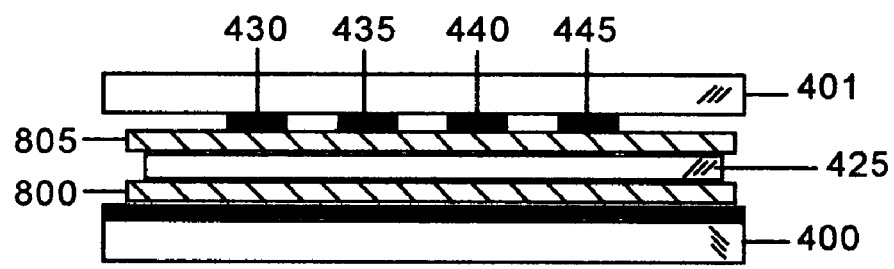

Used During Electrophoretic Separation—Description and Operation—FIGS. 12 and 13

During an electrophoretic separation, a large electrical potential difference is applied across the area of gel 425. Conductors parallel to conductor 420, oriented parallel to the potential gradient vector, will cause the potential difference from one end of the gel to the other to be zero. This can be remedied with the insertion of an insulator 800 between electrodes parallel to electrode 420 and gel 425, as shown in FIG. 12.

Although not required for electrodes 430-445, a similar insulator 805 can be inserted between these electrodes and gel 425 (FIG. 13).

Insulators 800 and 805 are preferably made of a material called parylene. Parylene is a vapor-deposited polymer comprising para-xylene, well-known to those skilled in the art of coating materials. This material has very high dielectric strength, typically 275 volts/micron. Thus, in very thin layers, it can resist breakdown at the potential applied in most electrophoretic separation procedures. Parylene coatings are available from various vendors, including Para Tech Coatings, Inc., of Aliso Viejo, Calif., USA.

With insulator 800 or insulators 800 and 805 in place, the instant system can collect dielectric constant data during an electrophoretic separation. The separation is not disturbed. Thus, monitor 635 can display the separation in progress.

With this method, the gel can be surveyed prior to separation using the instant system. Small variations in dielectric constant of the gel, due to incomplete mixing, thickness variations, and the like, can be stored as data and later subtracted from the data obtained during or after the separation.

In a gradient gel, the dielectric constant of the gel material may change in the direction of separation. By applying the above pre-run calibration step, the gradient of the gel can be taken into consideration and later subtracted from the separation data.

SUMMARY, RAMIFICATIONS, AND SCOPE

Thus it is seen that I have provided an improved method and apparatus for visualizing electrophoretic separations. Stains, radioactive, and fluorescent materials are not required, but can still be used.

While the above description contains many specificities, these should not be considered limiting but merely exemplary. Many variations and ramifications are possible.

Instead of a display, results can be printed, tabulated, or sent to a remote location for review. Instead of gray scale representation, colors can be used to show the location of bands. Materials, sizes, shapes, voltages, and other parameters can be changed. The output of the detection system can be indicated by sound, printout, stored values, different colored lamps or bands, and the like.

While the present system employs elements that are well-known to those skilled in the arts of computer software and hardware design, it combines these elements in a novel way which produces a new result not heretofore discovered. Accordingly the scope of this invention should be determined, not by the embodiments illustrated, but by the appended claims and their legal equivalents.

I claim:

1. A system for detecting and displaying two-dimensional images of electrophoretic separations of constituents of a substance in a gel said constituents being capable of changing the electrical impedance within said gel, comprising:

a computer, a gel having first and second sides, a first insulating plate fitted with a first plurality of parallel, linear electrodes adjacent said first side of said gel, a second insulating plate fitted with a second plurality of parallel, linear electrodes adjacent said second side of said gel, said first plurality of linear electrodes adjacent said first side of said gel being oriented orthogonally with respect to said second plurality linear electrodes adjacent said first side of said gel so that at least one of said electrodes adjacent said second side of said gel overlaps at least one of said electrodes adjacent second side of said gel, said first and said second insulating plates being fixed in position relative to one-another during use and separable at other times, a voltage source arranged to be connectable sequentially and capable of applying a voltage to first plurality of parallel, linear electrodes adjacent said first side of said gel, an amplifier arranged to be connectable sequentially to second plurality of parallel, linear electrodes adjacent said second side of said gel and capable of sensing changes in electrical impedance at a location where said first and second plurality of electrodes overlap and reporting said changes to said computer, whereby said changes in electrical impedance can be recorded and displayed by said computer.

2. The system of claim 1, wherein at least one of said first and second pluralities of electrodes is in contact with said gel.

3. The system of claim 1, further including a first insulating layer interposed between said gel and said first plurality of electrodes on said first insulating plate.

4. The system of claim 1, further including a second insulating layer interposed between said gel and said second plurality of electrodes on said second insulating plate.

5. The system of claim 1, wherein said electrophoretic separation is selected from the group consisting of a separation in progress and a completed separation.

6. The system of claim 1, having an output provided on a plurality of humanly sensible indicia selected from the class consisting of visual displays, sounds, and printouts.

7. A method for imaging electrophoretic separations of a substance in a gel where said substance contains a plurality of separable constituents, comprising:
   providing a gel having first and second sides and prepared for a separation,
   providing a substance for separation,
   providing a first insulating plate fitted with a plurality of parallel, linear electrodes adjacent said first side of said gel,
   providing a second insulating plate fitted with a plurality of parallel, linear electrodes adjacent said second side of said gel, said electrodes adjacent said second side of said gel being oriented orthogonally with respect to said electrodes adjacent said first side of said gel so that at least one of said electrodes adjacent said first side of said gel overlaps at least one of said electrodes adjacent said second side of said gel,
   said first and said second insulating plates being fixed in position relative to one-another during use and separable at other times,
   providing a voltage source,
   applying voltage from said source sequentially to each of said plurality of parallel, linear electrodes adjacent said first side of said gel,
   providing an amplifier arranged to sense changes in electrical impedance where said electrodes adjacent said first side of said gel and said electrodes adjacent said second side of said gel overlap,
   connecting said amplifier sequentially to each of said electrodes adjacent said second side of said gel so that at least one of said electrodes adjacent said second side of said gel overlaps at least one of said electrodes adjacent said first side of said gel,
   providing a computer arranged to receive, record, and display said changes in said electrical impedance,
   substance into said constituents within said gel, and
   sensing, recording, and displaying differences in electrical properties between said gel in the presence of said constituents and said gel in the absence of said constituents, and displaying the locations of said constituents in said substance within said gel,
   whereby said electrophoretic separation of said substance is imaged.

8. The method of claim 7, further including separating said substance into said constituents and detecting and displaying the loci of said constituents in said substance after the process of separating is complete.

9. The method of claim 7, further including providing an insulator over at least one of said first plurality of electrodes on said first insulating plate, one of said second plurality of electrodes on said second insulating plate, or both.

10. The method of claim 7, further including displaying the locations of said constituents in said substance during the process of separation.

11. The method of claim 7, further including storing a first set of data comprising the electrical properties of said gel before said separation, then storing a second set of data comprising the electrical properties of said gel after said separation, and comparing said first and said second sets of data.

12. Apparatus for detecting, recording, and displaying one-dimensional and two-dimensional images of electrophoretic separations of migratory materials in a gel, comprising:
   a gel having first and second sides and containing said migratory materials,
   a first insulating plate fitted with a first plurality of parallel, linear electrodes adjacent said first side of said gel,
   a second insulating plate fitted with a second plurality of parallel, linear electrodes adjacent said second side of said gel, said second plurality of linear electrodes adjacent said second side of said gel being oriented orthogonally with respect to said first plurality of linear electrodes adjacent said first side of said gel,
   said first and said second insulating plates being fixed in position relative to one-another during use and separable at other times,
   a voltage source sequentially connected to said first plurality of electrodes on said first plate by a first multiplexing means,
   a sample-and-hold means,
   an analog-to-digital converter means,
   an amplifier sequentially connected to said first plurality of electrodes on said second plate by a second multiplexing means, said amplifier, in combination with said sample-and-hold means and said analog-to-digital converter means, being capable of detecting differences in electrical properties between said gel and said materials for each pair of electrodes selected by said first and said second multiplexing means,
   a computer arranged to control said voltage source, said sample and hold means, said analog-to-digital converter means, and said first and said second multiplexing means and to monitor, report, and display differences in said electrical properties between said separated materials within said gel,
   whereby said differences in said electrical properties representative of said separations are detected, recorded, and displayed by said computer.

13. The apparatus of claim 12, wherein at least one of said first plurality or said second plurality of electrodes is in contact with said gel.

14. The apparatus of claim 12, further including an insulating layer interposed between at least one of said first plurality of said second plurality or electrodes and said gel.

15. The apparatus of claim 12, further including providing an output on a plurality of humanly sensible indicia selected from the class consisting of visual displays, sounds, and printouts.

* * * * *